(12) United States Patent
Sakai et al.

(10) Patent No.: US 6,879,392 B2
(45) Date of Patent: Apr. 12, 2005

(54) METHOD AND APPARATUS FOR INSPECTING DEFECTS

(75) Inventors: Kaoru Sakai, Yokohama (JP); Shunji Maeda, Yokohama (JP); Takafumi Okabe, Yokohama (JP); Masahiro Watanabe, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/115,880

(22) Filed: Apr. 2, 2002

(65) Prior Publication Data

US 2003/0025904 A1 Feb. 6, 2003

(51) Int. Cl.⁷ .............................................. G01N 21/88
(52) U.S. Cl. .............................. 356/237.4; 356/237.5; 250/559.45
(58) Field of Search ................. 356/237.1, 237.2–237.5, 356/239.1–239.8, 600, 394; 250/559.39, 559.4–559.49; 382/145, 149

(56) References Cited

U.S. PATENT DOCUMENTS 5,963,314 A * 10/1999 Worster et al. ............ 356/237.2
6,539,106 B1 * 3/2003 Gallarda et al. ............ 382/149

FOREIGN PATENT DOCUMENTS

JP          2000-161932       6/2000
JP          2000-193594       7/2000

* cited by examiner

Primary Examiner—Richard A. Rosenberger
Assistant Examiner—Vincent P. Barth
(74) Attorney, Agent, or Firm—Townsend and Townsend and Crew LLP

(57) ABSTRACT

In a defect inspecting apparatus, having contrast, brightness and appearance of a target for inspection and detection sensitivity of a defect changed depending on optical system conditions, and adapted to perform inspection by selecting an optimal test condition, even an unskilled user can easily select an optimal optical condition by quantitatively displaying evaluation values side by side when optical system conditions are changed. Moreover, by selecting an evaluation item having highest satisfaction based on a result of a series of test inspection, an optimal test condition can be automatically selected.

19 Claims, 10 Drawing Sheets

TEST CONDITION 1

IMAGE

CONTRAST × ×
DENSITY DIFFERENCE × ×

LUMINANCE
DISTRIBUTION

VARIANCE IN DENSITY × ×
DIFFERENCE OF
NORMAL PORTION

FIG. 3
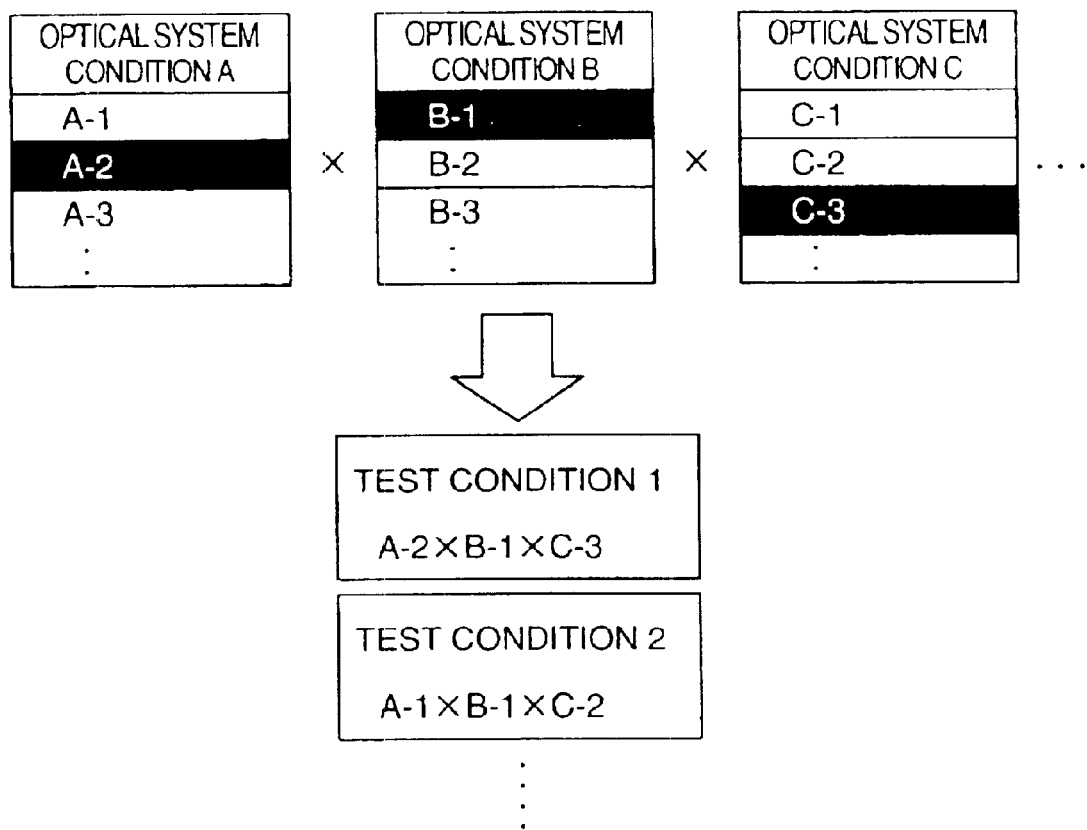
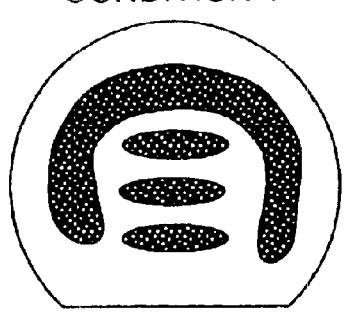
FIG. 4A
TEST CONDITION 1
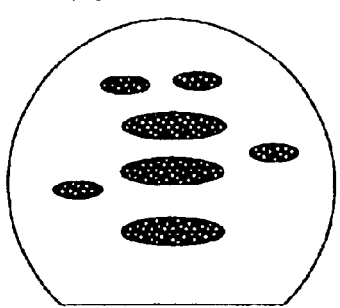
FIG. 4B
TEST CONDITION 2
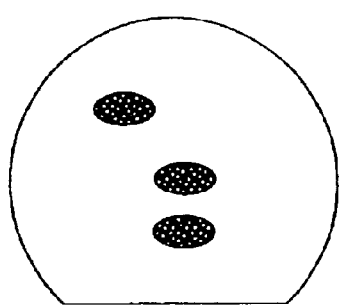
FIG. 4C
TEST CONDITION 3

FIG. 5A

TEST CONDITION 1

IMAGE

CONTRAST × ×
DENSITY DIFFERENCE × ×

LUMINANCE
DISTRIBUTION

VARIANCE IN DENSITY × ×
DIFFERENCE OF
NORMAL PORTION

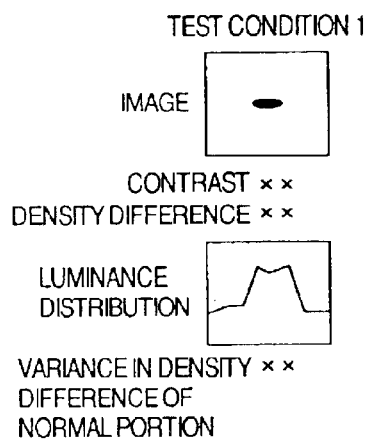

FIG. 5B

TEST CONDITION 2

IMAGE

CONTRAST × ×
DENSITY DIFFERENCE × ×

LUMINANCE
DISTRIBUTION

VARIANCE IN DENSITY × ×
DIFFERENCE OF
NORMAL PORTION

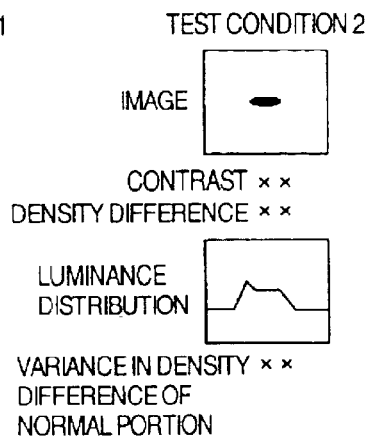

FIG. 5C

TEST CONDITION 3

IMAGE

CONTRAST × ×
DENSITY DIFFERENCE × ×

LUMINANCE
DISTRIBUTION

VARIANCE IN DENSITY × ×
DIFFERENCE OF
NORMAL PORTION

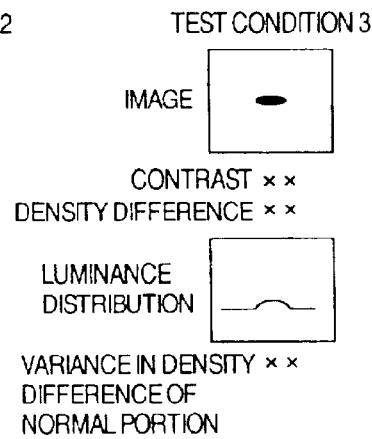

FIG. 6A

TEST CONDITION 1

IMAGE

CONTRAST × ×
BRIGHTNESS × ×

LUMINANCE
DISTRIBUTION

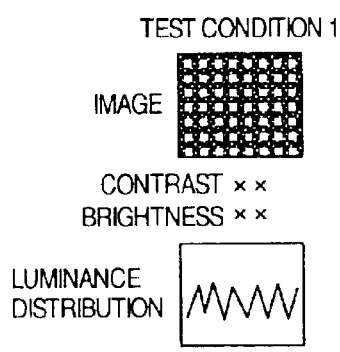

FIG. 6B

TEST CONDITION 2

IMAGE

CONTRAST × ×
BRIGHTNESS × ×

LUMINANCE
DISTRIBUTION

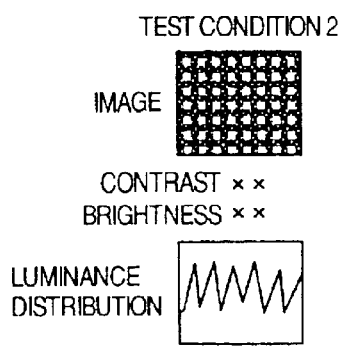

FIG. 6C

TEST CONDITION 3

IMAGE

CONTRAST × ×
BRIGHTNESS × ×

LUMINANCE
DISTRIBUTION

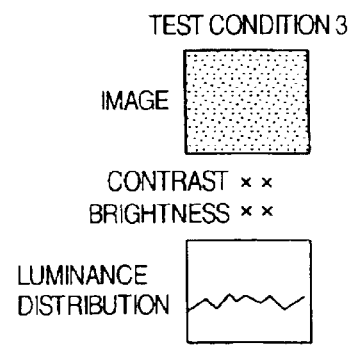

TEST CONDITION 1

| NUISANCE DEFECT | *% |
| FOREIGN OBJECT | **% |
| SHAPE FAILURE | **% |
| SCRATCH | **% |
| . | |
| . | |
| . | |

TEST CONDITION 2

| NUISANCE DEFECT | *% |
| FOREIGN OBJECT | |
| SHAPE FAILURE | |
| SCRATCH | |
| . | |
| . | |
| . | |

TEST CONDITION 3

| NUISANCE DEFECT | *% |
| FOREIGN OBJECT | |
| SHAPE FAILURE | |
| SCRATCH | |
| . | |
| . | |
| . | |

METHOD AND APPARATUS FOR INSPECTING DEFECTS

CROSS REFERENCE TO RELATED APPLICATION

This application is related to and claims priority from Japanese Application No. 2001-104153, filed Apr. 3, 2001.

BACKGROUND OF THE INVENTION

The present invention relates to a method and an apparatus for inspecting defects, capable of inspecting defects such as foreign objects, shape failures and scratches on a substrate to be inspected, e.g., a semiconductor wafer, with high sensitivity by using light or a charged particle beam.

In a defect inspecting apparatus, optical inspection and SEM inspection both include pluralities of conditions: a deflection condition, a wavelength region and the like for the former, and an acceleration voltage, a beam current, the number of scanning times and the like for the latter. Depending on combinations thereof, the number of settable conditions even reaches several tens. One among these conditions is selected to provide highest inspection sensitivity, and then inspection is carried out.

As the conventional art regarding a method of setting optical or charged particle conditions in the defect inspecting apparatus, technologies described in JP-A-12-161932 (conventional art 1) and JP-A-2000-193594 (conventional art 2) have been known.

The conventional art 1 includes means for irradiating a substrate surface having a circuit pattern formed with light, or light and a charged particle beam, means for detecting a signal generated from the substrate, means for converting the signal detected by the detecting means into an image and temporarily storing the image, means for comparing a region of the stored image with another region having an identical circuit pattern formed, inspecting means for determining defects on the circuit pattern based on a result of the comparison, and a region for displaying operation contents or input contents on operation screens for inspection and inspection condition setting. In this case, a screen hierarchy is set for displaying the operation screens in parallel, and an inspection condition is decided by using the screen hierarchy.

The conventional art 2 is directed to a circuit pattern inspecting method designed to detect pattern defects by irradiating a substrate surface having a circuit pattern formed with light or a charged particle beam, detecting a signal generated from the substrate surface by the irradiation, storing the detected signal as a digital image, comparing the stored image with an image expected to be identical thereto to extract a difference, and then displaying the difference extracted based on the comparison. In this case, an image of a region specified on the substrate surface is detected and stored as a digital image. For the stored digital image, comparison is made once or a plurality of times by changing conditions to extract a difference. A condition of comparison that enables a difference to be extracted is searched by determining a proper image processing condition based on a result of the extraction. The searched condition is stored. Then, by using the stored condition, a defect is extracted based on comparison, and an image of a defect portion extracted by the comparison is displayed.

As described in the above conventional art, in the defect inspecting apparatus, in inspection, a number of test conditions including optical system conditions for obtaining an image and an image processing parameter for detecting defects from the obtained image are generally set to be optimal for each target for inspection as shown in FIG. 13.

First, in the defect inspecting apparatus, a given optical system condition is set (S1301). An optical image is detected from a pattern to be inspected with particularly high sensitivity under the set optical system condition (S1302). The detected optical image is displayed on displaying means, and a user visually verifies whether contrast or brightness of the displayed optical image is sufficient or not (S1303). These steps are repeated a plurality of times while changing the optical system conditions. A plurality of optical system conditions are present and, if combinations thereof are included, the number thereof becomes enormous. Thus, the user narrows down the optical system conditions to a plurality of test conditions having sufficient contrast and brightness of the optical image (S1304). Then, an image processing parameter is set (S1305), and test inspection is carried out in a small region (S1306). Then, for each detected defect candidate, verification is made as to whether the defect is one to be originally detected, or it was erroneous detection (S1307). These steps are carried out for all the selected test conditions (S1308), and one optical system condition having a largest number of detected defects and least erroneous detection is decided (S1309).

Subsequently, similarly to the optical system condition, the image processing parameter is set all over again (S1310), and test inspection (S1311) and detection rate checking (S1311) are repeated until sensitivity becomes sufficient (S1313). Then, after an optimal image processing condition is set, inspection is carried out (S1314).

In the above-described method of setting test conditions (inspection conditions), the process is basically sensual evaluation by the visual verification of the user. Consequently, a rule of thumb or skills are necessary, and individual differences occur in setting results. Furthermore, when the test conditions are narrowed down, the test conditions for realizing high sensitivity are not necessarily included. Since setting of the test conditions and the visual verification are repeated, binding hours for test condition setting become enormous for the user.

SUMMARY OF THE INVENTION

In order to solve the foregoing problems, an object of the present invention is to provide a method and an apparatus for inspecting defects, capable of reducing binding hours for a user, selecting an optimal test condition, and always achieving highly sensitive defect inspection.

Another object of the present invention is to provide a method and an apparatus for inspecting defects, capable of reducing sensitivity errors between defect inspecting apparatus.

In order to achieve the above-described objects, the present invention provides a method and an apparatus for inspecting defects, adapted to perform a series of test inspection for detecting one of light, a secondary electron, a reflected electron, a transmitted electron and an absorbed electron generated from a substrate to be inspected by irradiating the substrate to be inspected with light or a charged particle beam, converting the detected one into an image signal, and discovering a defect portion on the substrate to be inspected based on a digital image signal obtained by subjecting the converted image signal to A/D conversion, while changing a plurality of test conditions, each being composed of a plurality of optical system conditions set beforehand.

In the method and the apparatus for inspecting defects, as a result of the series of test inspection, bits of information of the defect portion discovered on the substrate to be inspected under the respective test conditions are presented side by side for the plurality of test conditions.

In the method and the apparatus for inspecting defects, as a result of the series of test inspection, bits of information of the defect portion discovered on the substrate to be inspected under the respective test conditions are presented side by side for the plurality of test conditions, and an optimal test condition is selected based on the presented bits of information of the defect portion.

In the method and the apparatus for inspecting defects, as a result of the series of test inspection, bits of information regarding digital image signals of a specified region among the digital image signals obtained under the respective test conditions are presented side by side for the plurality of test conditions.

In the method and the apparatus for inspecting defects, as a result of the series of test inspection, bits of information regarding digital image signals of a specified region among the digital image signals obtained under the respective test conditions are presented side by side for the plurality of test conditions, and an optimal test condition is selected based on the presented bits of information regarding the digital image signals of the specified region.

In the method and the apparatus for inspecting defects, as a result of the series of test inspection, the defect portion including a nuisance defect (or a false defect) is classified based on the digital image signal of the defect portion discovered under each test condition, and results of the classification are presented side by side for the plurality of test conditions.

In the method and the apparatus for inspecting defects, as a result of the series of test inspection, a true defect part and a nuisance defect are identified based on the digital image signal of the defect portion discovered under each test condition, and results of the identification are presented side by side for the plurality of test conditions.

In the method and the apparatus for inspecting defects, as a result of the series of test inspection, a true defect part and a nuisance defect are identified based on the digital image signal of the defect portion discovered under each test condition, and the identified test condition having a low nuisance defect ratio is selected.

In the method and the apparatus for inspecting defects, the information of the defect portion is represented by a defect map indicating a defect portion distribution.

In the method and the apparatus for inspecting defects, coincidence of defect portions between the test conditions is further presented.

In the method and the apparatus for inspecting defects, the information of the defect portion is a combination of a plurality of any selected from an image, contrast, brightness or a density difference, and a luminance distribution of a specified defect portion.

In the method and the apparatus for inspecting defects, bits of information regarding digital image signals in a specified region among digital image signals obtained under the respective test conditions are further presented side by side for a plurality of test conditions.

In the method and the apparatus for inspecting defects, the information regarding the digital image signal in the specified region is a combination of a plurality of any selected from an image, contrast, brightness and a luminance distribution.

In the method and the apparatus for inspecting defects, the specified region is a region for inspecting a defect portion with high sensitivity.

In the method and the apparatus for inspecting defects, satisfaction with an evaluation item under the selected optimal test condition is further presented.

In the method and the apparatus for inspecting defects, inspection performance is further presented in real time during inspection after the selection of the optimal test condition.

The present invention is advantageous in that binding hours of a user for setting test conditions can be reduced, even an unskilled user can easily and surely select an optimal test condition, and defect inspection with high sensitivity can always be achieved without any individual differences.

Other objects, features and advantages of the present invention will become apparent upon reading of the following description of the preferred embodiments of the invention in conjunction with the accompanying drawings.

BRIEF DESCRIPTION OF THE DRAWINGS

FIG. 3 is a view showing an embodiment of optical system condition setting for test conditions according to the invention.

FIGS. 4A to 4C are views, each showing an embodiment of defect map displaying by test inspection according to the invention.

FIGS. 5A to 5C are views, each showing an embodiment of quantitative evaluation value displaying of a specified defect by test inspection according to the invention.

FIGS. 6A to 6C are views, each showing an embodiment of quantitative evaluation value displaying of a specified region by test inspection according to the invention.

DESCRIPTION OF THE EMBODIMENTS

Next, description will be made in detail for the embodiments of a defect inspecting apparatus according to the present invention with reference to FIGS. 1 to 12.

Figure 1:
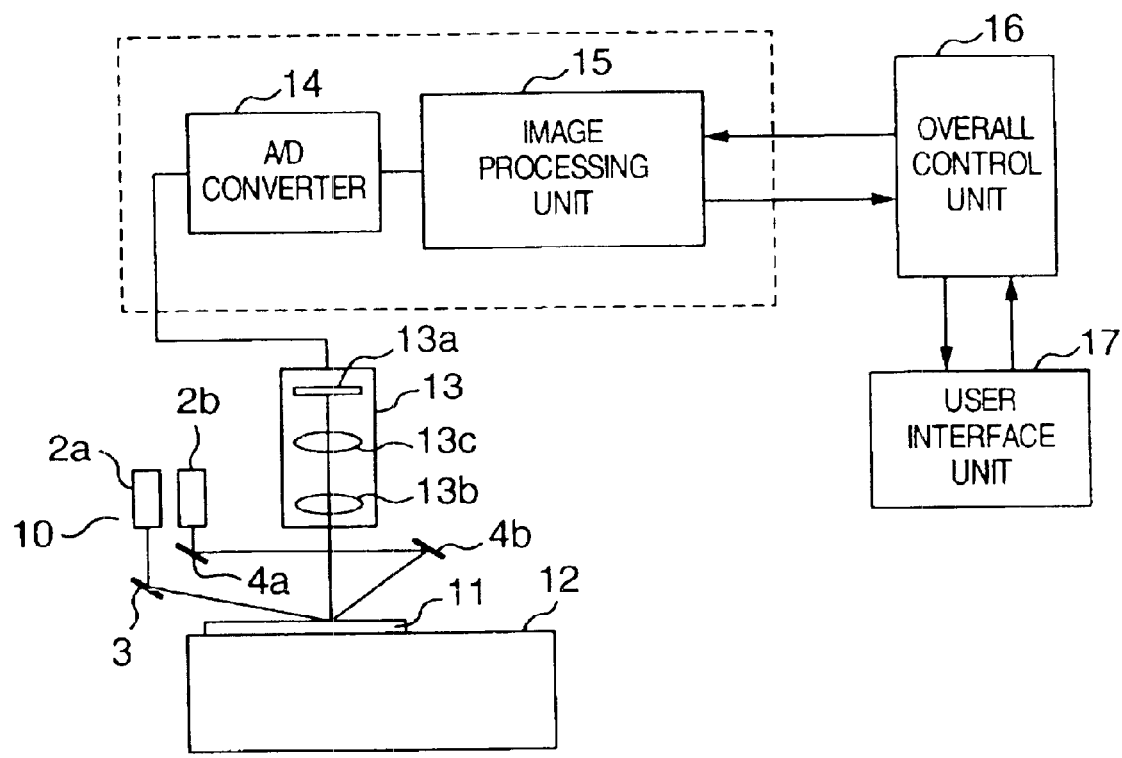
FIG. 1 is a schematic configuration view showing a bright field optical inspection apparatus as an embodiment of a defect inspecting apparatus according to the present invention.

FIG. 1 shows a configuration of a bright field optical inspection apparatus as an embodiment of a defect inspecting apparatus according to the invention, where a semiconductor wafer is a target for inspection. The bright field optical inspection apparatus includes: a stage 12 for fixing and moving a semiconductor wafer 11 to be inspected; an illumination optical system 10 for illuminating the semiconductor wafer 11 with UV light or DUV light in a very shallow oblique direction (low angular direction) or a substantially vertical direction (high angular direction) without any physical passage through an objective lens; a detection optical system 13 composed of an objective lens 13b for converging an optical image from the semiconductor wafer 11 illuminated by the illumination optical system 10, an imaging lens 13c for imaging the optical image converged by the objective lens, and a detector 13a such as a CCD or a TDI sensor for capturing the optical image imaged by the imaging lens and converting the image into an image signal; an A/D conversion circuit 14 for digitizing an output signal from a detector 13a of the detection optical system 13; an image processing unit 15 for detecting a defect by comparing two images obtained from the A/D conversion circuit 14 with each other; an overall control unit 16; and a user interface unit 17 for displaying an output result, an intermediate result or inspection information and accepting an entry from a user.

The illumination optical system 10 can be composed of, for example, a laser source 2a for emitting a laser light of 488 nm or 365 nm, and a laser source 2b for emitting a DUV laser light or a KrF excimer laser light of a double (532 nm) or quadruple (266 nm) wave of a YAG laser. A laser beam emitted from the laser source 2a is reflected by a mirror 3, and made incident on a surface of the semiconductor wafer 11 at a very shallow angle of 30° or lower (low angle). On the other hand, a laser beam emitted from the laser source 2b is reflected by a mirror 4a, further reflected by a mirror 4b, and then made incident on the surface of the semiconductor wafer 11 at a nearly vertical high angle. Illumination at such a high angel becomes pseudo annular illumination. If one laser source 2b is provided as a laser source, it is only necessary to provide an optical path switching mechanism for switching an emitted laser light to the mirror 4b and the mirror 3.

For each of the laser sources 2a and 2b, an optical system capable of controlling emitted laser power is provided. As a result, an arrangement is made to enable power of a laser beam, which is irradiated at a low or high angle to the surface of the semiconductor wafer 11, to be changed as an optical system condition. Thus, by changing the power of the laser light as the optical system condition, it is possible to adjust contrast and sensitivity.

In the detection optical system 13, if the laser sources 2a and 2b are both used, wavelength separation must be performed by using a wavelength separation beam splitter, and light images of the separated wavelengths must be detected by the detectors 13a. However, if the laser sources 2a and 2b are operated by different timings, a beam splitter and a plurality of detectors 13a need not be provided. In the detection optical system 13, for example an optical system capable of varying imaging magnification as an optical system condition is provided. Thus, by changing imaging magnification as the optical system condition, resolution can be adjusted. In addition, in the detection optical system 13, if a variable special filter is provided to shut off interference light obtained from edges of repeated circuit patterns, pitches and shapes of patterns formed to be variably controlled in the variable special filter may be set as optical system conditions. Thus, by adjusting the variable special filter as the optical system condition, it is possible to adjust noise reduction level.

Another optical system condition is a moving speed of the stage 12 for continuously moving the semiconductor wafer 11. If the detector 13a is composed of a TDI sensor or the like, yet another conceivable optical system condition is a scanning speed for reading a stored pixel signal from the TDI sensor. Thus, by changing the moving speed of the stage 12 and the scanning speed for reading the stored pixel signal from the TDI sensor, it is possible to adjust a dynamic range and sensitivity of the TDI sensor.

As described above, the optical system conditions are conditions of the optical system for obtaining the image signal from the detector 13a.

Now, an operation thereof will be described. First, the overall control unit 16 controls the stage 12 to continuously move the semiconductor wafer 11. In synchronization with this operation, images of inspection regions in the wafer are sequentially captured by the detector 13a such as a CCD or a TDI sensor. The sensor of the detector 13a outputs an entered signal to the A/D conversion circuit 14. The A/D conversion circuit 14 converts an analog signal divided into a plurality of pieces and entered as a pixel signal into a digital signal, and enters the signal to the image processing unit 15. The image processing unit 15 performs defect detection based on the entered image signal, and transmits a result of the defect detection to the overall control unit 16. The overall control unit 16 displays the detected defect on the user interface unit 17.

Now, in the detector 13a of the detection optical system 13, an appearance of an image to be inspected is greatly changed depending on set values of optical system conditions for capturing the image of the region to be inspected such as a deflection condition, a wavelength region, power and magnification. Accordingly, in order to perform inspection with high sensitivity, optical system conditions must be set to optimal values. However, since the optimal values vary depending on a target, that is, depending on a structure of a circuit pattern or an operation step of the target, optimal values must be set as occasion demands.

Hereinafter, description will be made for an embodiment of a method for setting optical system conditions in the bright field optical inspection apparatus according to the invention.

Figure 2:
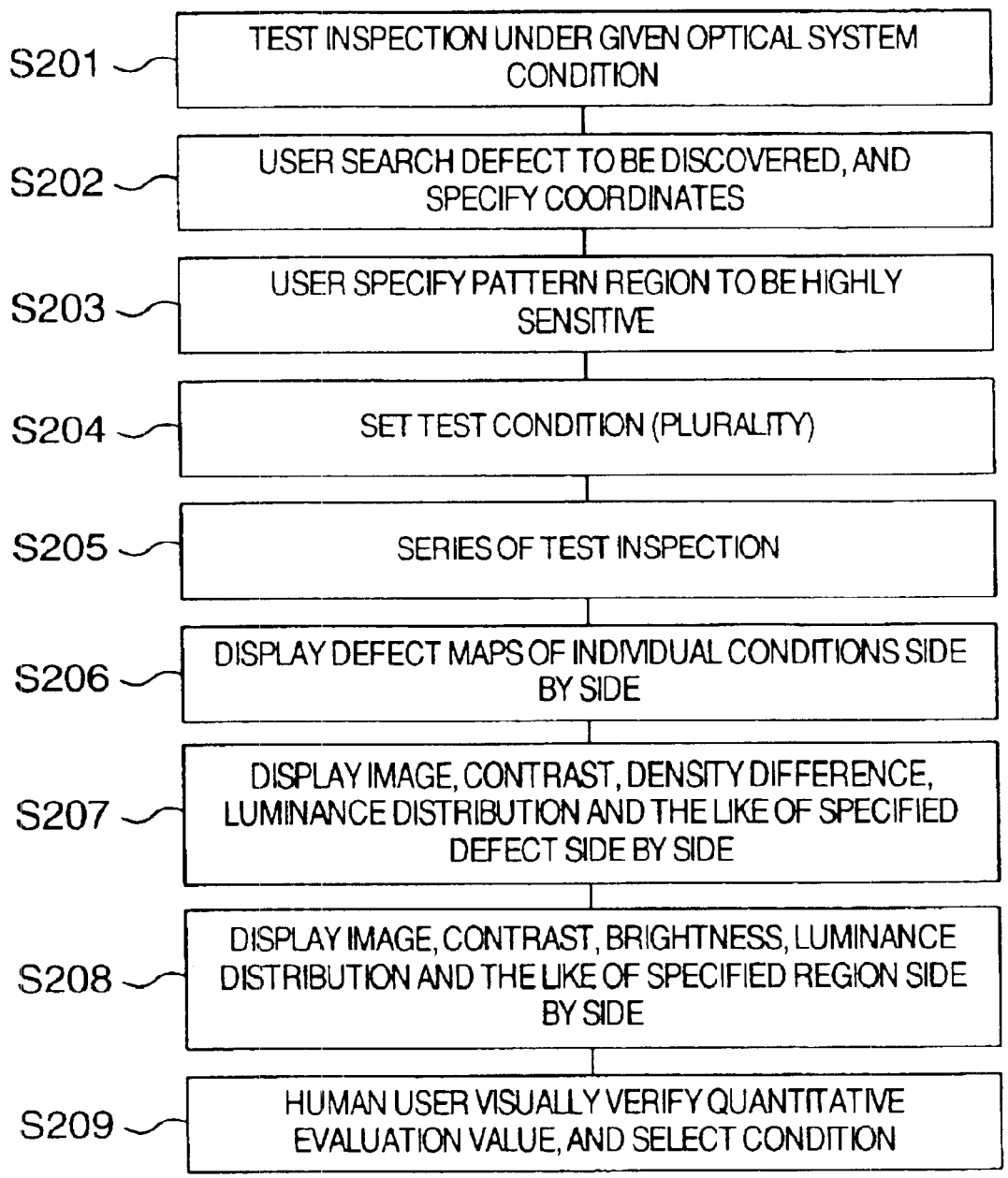
FIG. 2 is a flowchart showing an embodiment of optical system condition setting according to the invention.

FIG. 2 is a flowchart showing the embodiment of the method for setting optical system conditions in the bright field optical inspection apparatus of the invention.

As shown in FIG. 2, in the present invention, by using the bright field optical inspection apparatus, a user first carries out test inspection under given optical system conditions (deflection condition, wavelength region, power, magnification and the like) set to the overall control unit 16 (S201). The overall control unit 16 discovers a defect to be detected among defects detected by the image processing unit 15 under a rough condition, and coordinates of the defect is specified and entered through the user interface unit (display) 17 to the overall control unit 16 (S202). Also, a pattern region to be inspected with particularly high sensitivity such as a mat portion of the target for inspection, which is displayed on the screen of the display 17 or the like, is specified and entered to the overall control unit 16 (S203). In the image processing unit 15, as a method of discovering a defect under a rough condition, a defect (defect candidate) can be discovered by, for example comparing image signals obtained from the A/D converter 14 for respective chips repeated on the semiconductor wafer with each other to extract a difference image signal, and comparing the extracted difference image signal with a determination threshold value. Then, the overall control unit 16 displays the difference image signal of the defect detected by the image processing unit 15 or the defect image signal obtained from the A/D converter 14, so that coordinates of the defect can be specified on the screen. The coordinates of the defect may be automatically specified based on a feature quantity (area, shape and the like) of an image of the defect.

The overall control unit 16 displays design information in the chips arrayed on the semiconductor wafer on the display 17, the design information being obtained from a CAD system (not shown), for example through a network, so that a pattern region to be inspected with particularly high sensitivity such as a mat portion can be specified.

Then, the user selects one or more test conditions on the screen, each of which is in combination of a plurality of optical system conditions and is displayed on the display 17 or the like, and enters the selected test conditions to the overall control unit 16 (S204). In the embodiment, as shown in FIG. 3, an arrangement of optical system conditions for inspection includes combinations of levels 1, 2, 3, , , , of a plurality of optical system conditions A (e.g., laser power emitted from the laser source 2b and irradiated to the surface of the semiconductor wafer at a high angle), B (e.g., laser power emitted from the laser source 2a, and irradiated to the surface of the semiconductor wafer at a low angle), C (e.g., imaging magnification in the detection optical system 13), D (e.g., moving speed of the stage 12, and scanning speed for reading a stored pixel signal from the TDI sensor), and the like. Thus, the user enters and sets a plurality of test conditions (inspection conditions) having different combinations of optical system conditions to the overall control unit 16 beforehand, for example in a manner that as test condition (inspection condition) 1, a level of the optical system condition A (e.g., laser power emitted from the laser source 2b and irradiated to the surface of the semiconductor wafer at a high angle) is 2, a level of the optical system condition B (e.g., laser power emitted from the laser source 2a, and irradiated to the surface of the semiconductor wafer at a low angle) is 1, a level of the optical system condition C (e.g., imaging magnification in the detection optical system 13) is 3, as test condition (inspection condition) 2, a level of the optical system condition A is 1, a level of the optical system condition B is 1, and a level of the optical system condition C is 2, and the like.

The test conditions include image processing parameters for discovering defects or defect candidates from obtained image signal. A representative image processing parameter is determination threshold value for a difference image signal between a detected digital image signal obtained from the A/D converter 14 and a reference digital image signal.

Then, after completion of the test condition (inspection condition) setting by the user, a series of test inspection is carried out based on a command from the overall control unit 16 (S205). In the series of test inspection based on the command from the overall control unit 16, a small region including the defect and the pattern region specified by the user in S202 and S203 are sequentially inspected while automatically switching the set optical system conditions.

After completion of the series of test inspection, the overall control unit 16 displays defect maps obtained under the respective test conditions side by side on the user interface unit 17 (S206). As shown in each of FIGS. 4A to 4C, the defect map is the one that a place of the defects candidate detected by the image processing unit 15 is plotted corresponding to the inspected region in the test inspection. FIG. 4A shows an example of a number of defects detected on an outer periphery and the inside of the wafer under the test condition 1; FIG. 4B an example of not many defects detected on the outer periphery of the wafer under the test condition 2; and FIG. 4C an example of only a small number of defects detected inside the wafer under the test condition 3. The defects maps of FIGS. 4A to 4C are displayed side by side with a total number of defects generated on one semiconductor wafer 11. Thus, the user can determine an inspection condition for best defect detection at a glance. The overall control unit 16 can make a defect map and calculate a total number of defects based on defect coordinates specified for the defect detected by the image processing unit 15.

Further, the overall control unit 16 displays, as a result of the test inspection, an image, contrast, a density difference and a luminance distribution of the defect specified beforehand by the user, and variance in a density difference of a normal portion side by side (S207). FIGS. 5A to 5C show display examples thereof. Specifically, in FIGS. 5A to 5C, an image, contrast, a density difference and a graph of a luminance distribution of the specified defect, and variance in a density difference of a normal portion are displayed when detected under optical test conditions 1, 2 and 3, respectively. The contrast is represented by a quantitative value indicating a level of a luminance changing component that the defect has with respect to the peripheral portion thereof. The overall control unit 16 can calculate the contrast from an image including the specified defect obtained from the image processing unit 15. The density difference is represented by a difference value when comparison is made with a portion having no defects in the case of comparative inspection. The overall control unit 16 can obtain the density difference as a difference image signal from the image processing unit 15. The luminance distribution is shown by a graph, visually showing comparison between a quantity of light in the background and a quantity of light in the defect portion. The overall control unit 16 can calculate the luminance distribution from an image signal of the specified defect portion and the background obtained from the image processing unit 15.

As described above, the overall control unit 16 displays, as the result of the test inspection, the image, the contrast, the density difference and the luminance distribution of the defect specified beforehand by the user, and the variance in the density difference of the normal portion side by side on the user interface unit 17 as shown in FIGS. 5A to 5C. Thus, the user can quantitatively evaluate which optical system condition emphasizes the defect most.

Further, the overall control unit 16 displays (presents), as a result of the test inspection, an image, contrast, brightness and a luminance distribution of a region to be inspected with particularly high sensitivity, the region being specified beforehand by the user, side by side (S208). FIGS. 6A to 6C show display examples thereof. Specifically, in FIGS. 6A to 6C, an image, contrast, brightness, and a graph of a luminance distribution of the specified region are displayed when detected under optical test conditions 1, 2 and 3, respectively. The contrast is represented by a quantitative value indicating a level of a luminance changing component that the specified region has. The overall control unit 16 can calculate the contrast from the image of the specified region, which is obtained from the image processing unit 15. The brightness is represented by an average luminance value of the specified region. The overall control unit 16 can calculate the brightness by obtaining an average luminance value from an image signal of the specified region, which is obtained from the image processing unit 15. The luminance distribution is shown by a graph, visually showing a change in a quantity of light in the specified region. The overall control unit 16 can calculate the luminance distribution from the image signal of the specified region, which is obtained from the image processing unit 15.

As described above, the overall control unit 16 displays, as the result of the test inspection, the image, the contrast, the brightness and the luminance distribution of the region to be inspected with particularly high sensitivity, which is specified beforehand by the user, side by side on the user interface unit 17 as shown in FIGS. 6A to 6C. Thus, the user can quantitatively evaluate which optical system condition provides a sufficient quantity of light in the specified region.

Thus, in FIGS. 4A to 6C, not only the inspection results but also the actual test conditions (inspection conditions) are displayed. Then, the user selects a test condition based on the comparative displaying of the respective test conditions and the quantitative inspection results in this case (S209).

As described above, in the bright field optical inspection apparatus, if the user sets a combination of optical system conditions in the overall control unit 16 beforehand, a series of inspection is automatically carried out, and a result of the inspection is displayed on the user interface unit 17. Accordingly, the user can easily select an optimal test condition from an evaluation value. However, another embodiment is possible, where defect detection performances under the optical system conditions are further displayed (presented), and thus selection by the user can be more assured and facilitated.

Figure 7:
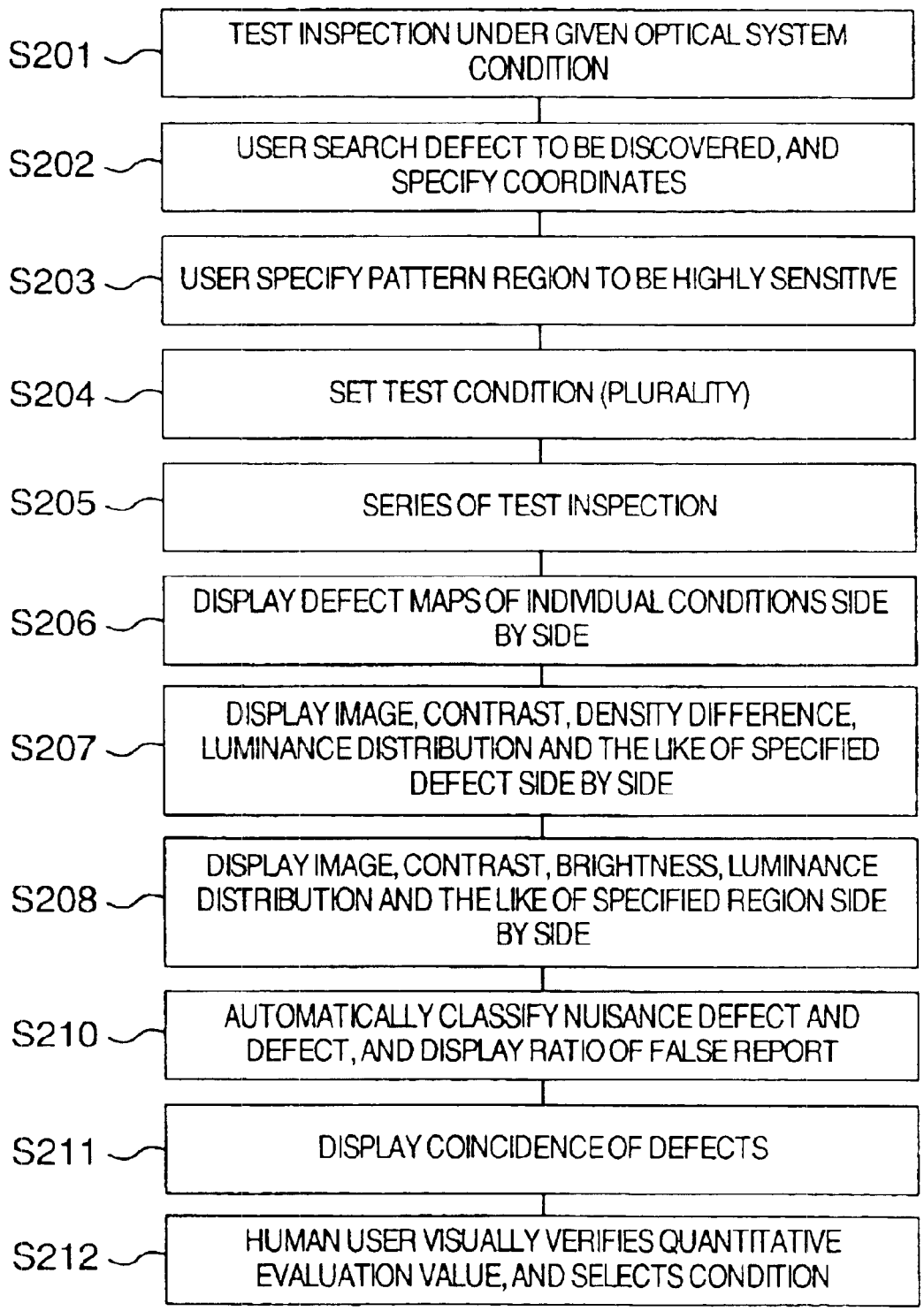
FIG. 7 is a flowchart showing an embodiment of optical system condition setting according to the invention.

FIG. 7 shows a flow of an embodiment of the above-described operation. S201 to S208 are similar to those of the embodiment of FIG. 2. The overall control unit 16 automatically classifies defect candidates detected by the image processing unit 15 under each optical condition, as defects and nuisance defects (or false defects), and calculates and displays a ratio of nuisance defects to the number of detected candidates on the user interface unit 17 (S210). In this case, the overall control unit 16 automatically classifies the defects as types (e.g., foreign object defect, shape defect of a circuit pattern, disconnection and short-circuiting of a wiring pattern, scratches on an insulating film when CMP is carried out, for example), and displays the types based on a correlation regarding a defect, such as a ratio K=H(i)/L(i) between an image signal H(i) at high angle illumination, and an image signal L(i) at low angel illumination, or a feature quantity (e.g., area, dimensions in a vector axis direction and a right-angle direction thereof, moment of a vector axis, a shape or the like), and displays the types. Especially, since the foreign object defect has a convex particle shape, K becomes small. In the case of a scratch, a shape is very shallow concave, and thus K becomes large. Accordingly, depending on K values, classification can be made for foreign objects and scratches. In the case of a pattern defect, classification can be made based on a feature quantity such as a shape.

Figure 8A:
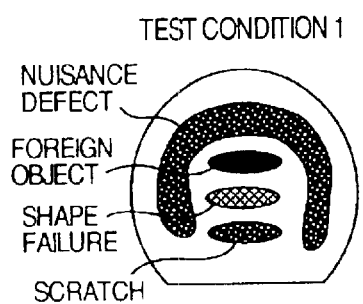
FIGS. 8A to 8C are views, each showing an embodiment of automatic classification result displaying of a nuisance defect (or a false defect) and a defect by test inspection according to the invention.
Figure 8B:
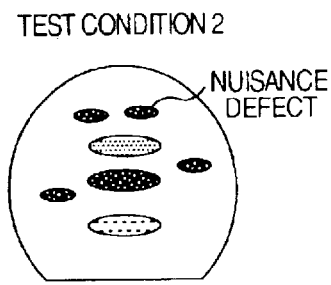
Figure 8C:
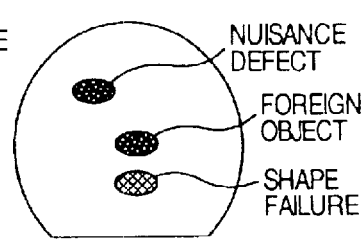
Figure 9:
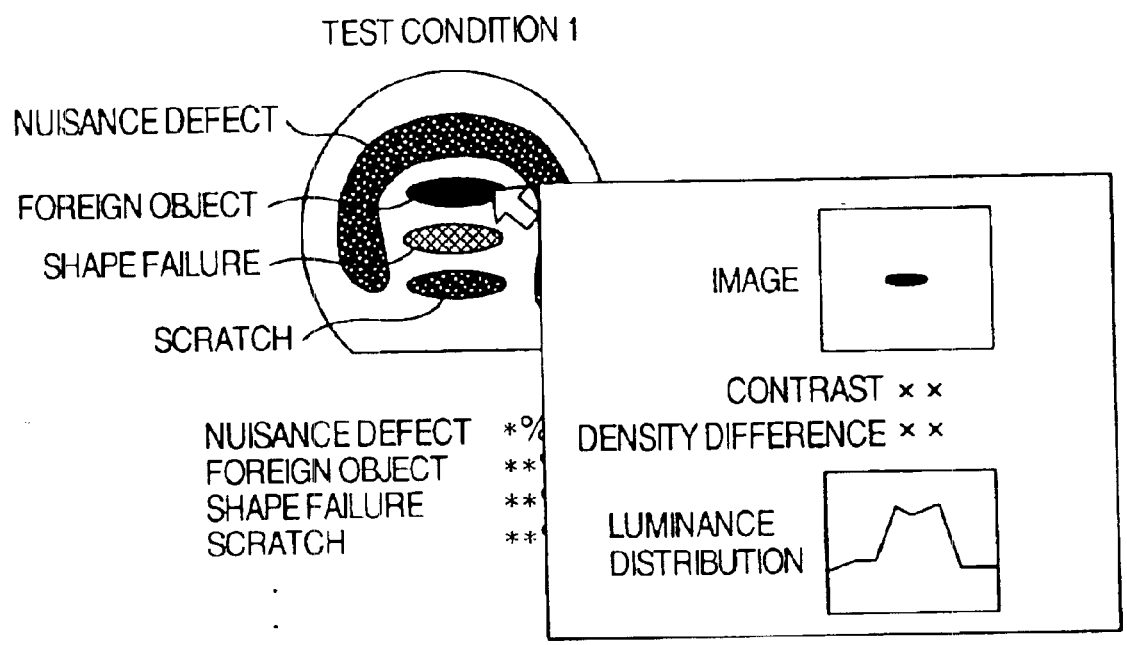
FIG. 9 is a view showing an embodiment of detailed information displaying of a defect detected by test inspection according to the invention.
Figure 10:
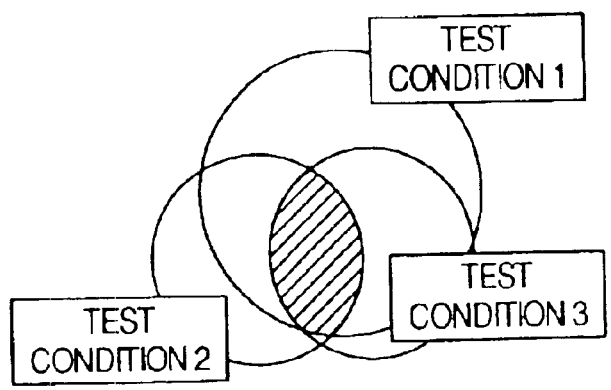
FIG. 10 is a view showing an embodiment of coincidence displaying of a defect by test inspection according to the invention.

FIGS. 8A to 8C show an embodiment of the above-described displaying. Specifically, in FIGS. 8A to 8C, classification results of defects (foreign object, shape failure, scratches and the like) and nuisance defects are respectively plotted when detected under the test conditions 1, 2 and 3 corresponding to inspection regions, and the nuisance defects and the defects, types of defects and a distribution thereof are displayed (presented) so as to be understood at a glance. In addition, the ratio of nuisance defects to a total number of detected defects, and the number or the ratio of defects of each type are also displayed. In order to see detailed contents of defects of each type, as shown in FIG. 9, a target portion is clicked by a mouse, and then detailed information of a defect (image signal, contrast, density difference and luminance distribution of the defect) as shown in FIGS. 5A to 5C is displayed in a pulled-down manner. Accordingly, types of defects seen under the respective optical system conditions and appearances thereof can be found at a glance. The overall control unit 16 also displays coincidence of defects between the test conditions based on the result of the classification (S211). FIG. 10 shows an example thereof. A defect (indicating coincidence of defects) detected in common under the respective test conditions is represented by a crossing portion of circles of the respective conditions (hatched portion in the drawing). The user compares defect detection performances with one another, selects an inspection condition on the user interface unit 17, and enters the selected inspection condition to the overall control unit 16 (S212). In other words, in step S212, the user (human being) visually verifies a quantitative evaluation value, selects an inspection condition to enter the selected condition to the overall control unit 16.

The embodiment for deciding the test condition (inspection condition) based on the quantitative evaluation value has been described. However, the user enters and sets an acceptance value of each quantitative evaluation value in the overall control unit 16 beforehand, and then the overall control unit 16 can automatically select an inspection condition that satisfies or is closest to the acceptance value.

Figure 11:
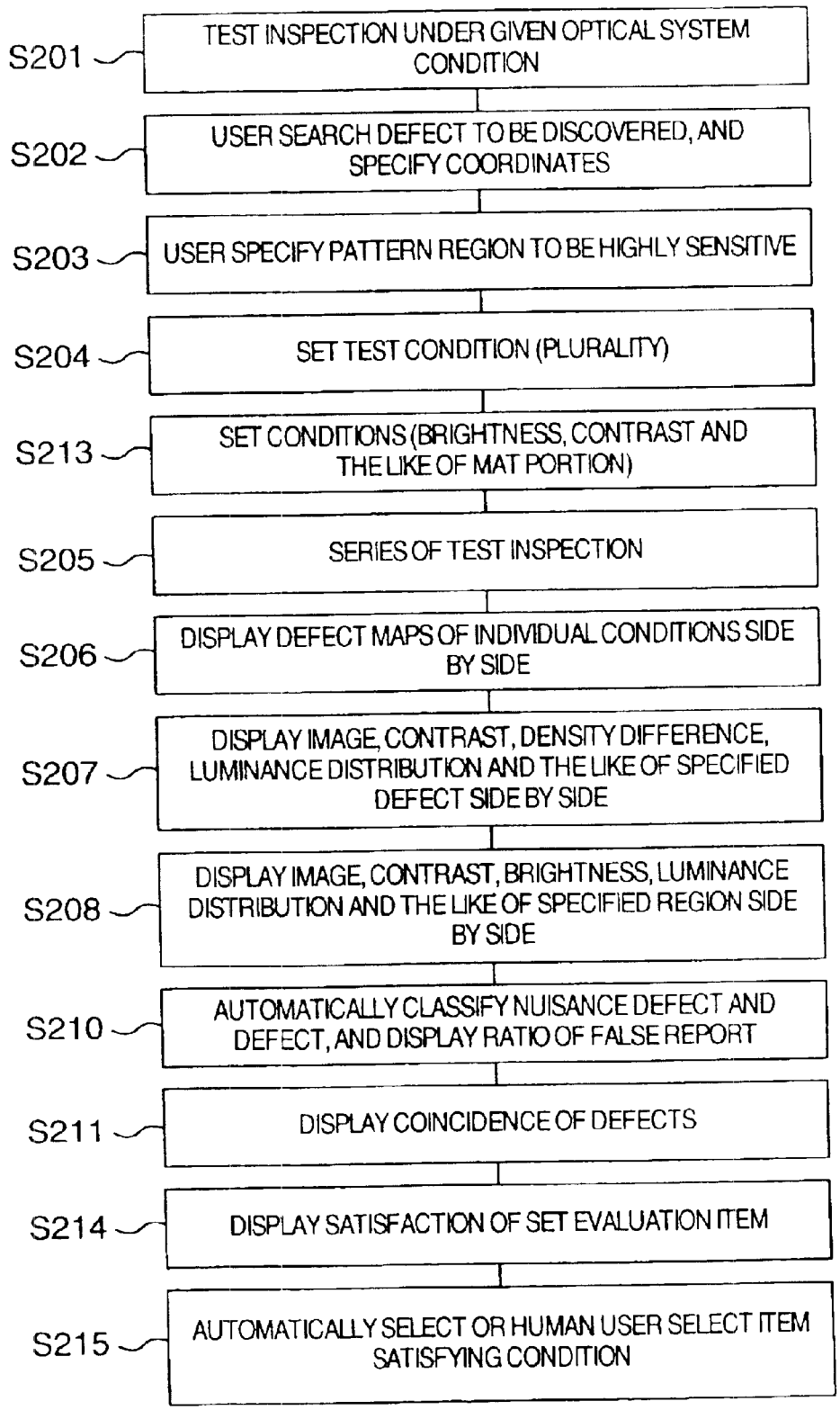
FIG. 11 is a flowchart showing an embodiment of optical system condition setting according to the invention.

FIG. 11 shows a flow of an embodiment of the above-described operation. For example, as shown in FIG. 11, S201 to S204 are similar to those of the previous embodiments. However, in the present embodiment, before test inspection, an acceptance value of each quantitative evaluation item (e.g., density difference of a defect is 25 or higher (determination threshold value), nuisance defect is 10% or lower, or the like) is entered and set in the overall control unit 16 (S213). That is, in step S213, brightness, contrast and the like of a pattern region (e.g., mat portion) to be inspected with higher sensitivity are entered and set as test conditions in the overall control unit 16. Such setting may be made for all items in the test condition or only specified items in the test condition.

Then, test inspection and result displaying (presentation) are carried out as in the cases of the previous embodiments (S205 to S211).

Figure 12:
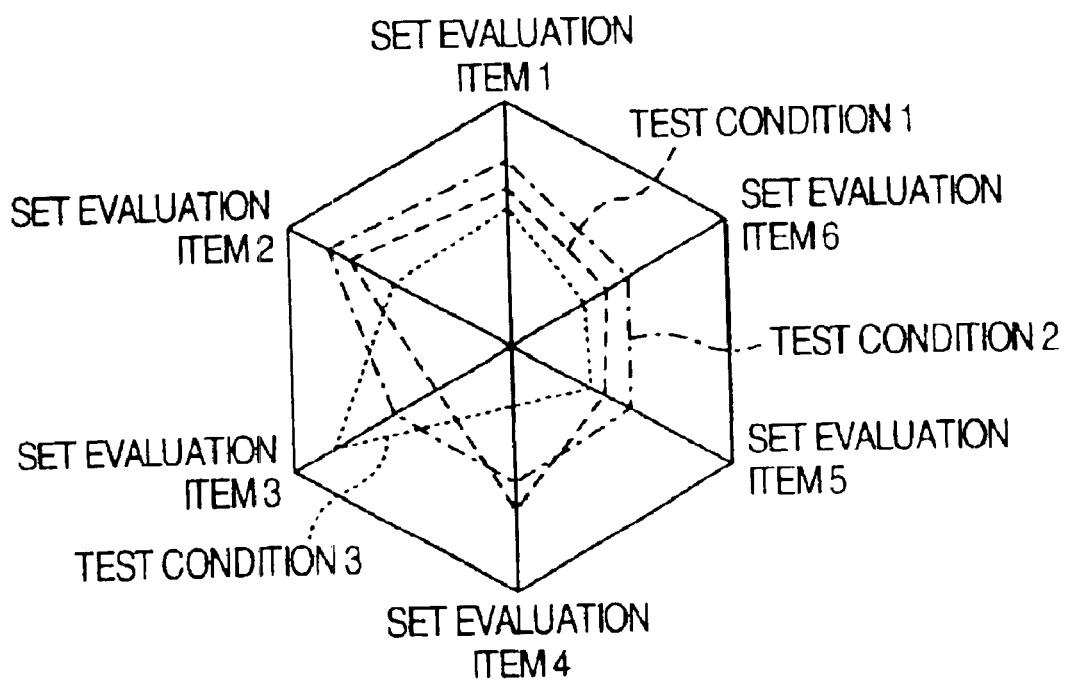
FIG. 12 is a view showing an embodiment of evaluation item satisfaction displaying by test inspection according to the invention.
Figure 13:
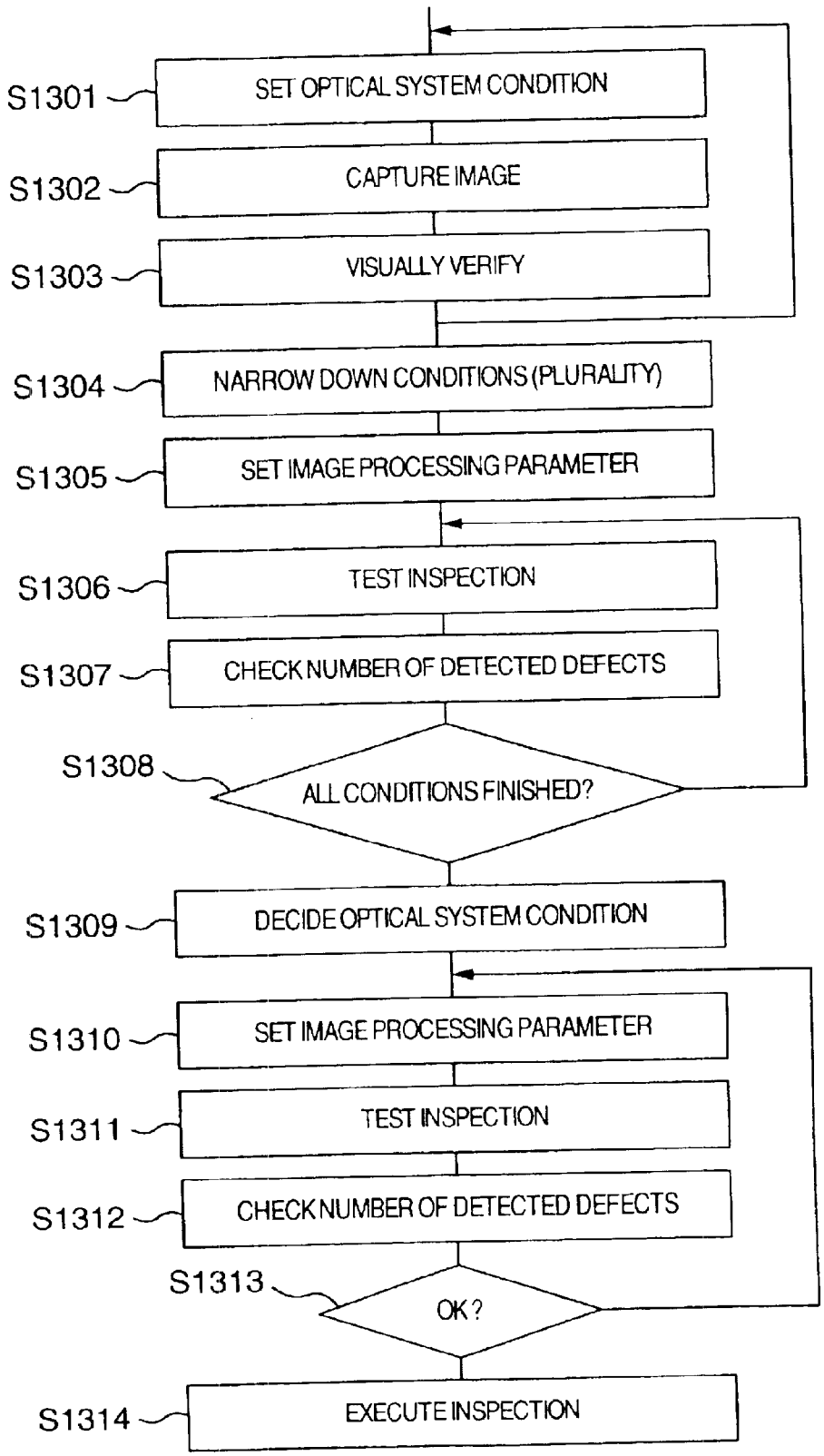
FIG. 13 is a flowchart showing test condition setting according to a conventional art.

Then, satisfaction degree with an acceptance value of a set evaluation item is displayed (presented) for each test condition (S214). FIG. 12 shows an embodiment of this operation. Here, acceptance values are set for five evaluation items, and it is shown by a radar chart how much a result of test inspection satisfies the acceptance value under each inspection condition. The user can decide an optimal condition based on such satisfaction, and the overall control unit 16 can automatically select a test condition having highest satisfaction (S215).

The embodiment for selecting an optimal condition from a plurality of test conditions set by the user has been described. However, in the present invention, a completely automatic operation can be performed from test condition setting. Specifically, test conditions set in the past, a wafer process thereof and the like are entered and stored as a database, for example, in a storage device or a memory (not shown) connected to the overall control unit 16. When conditions of the wafer of the same process are established, a series of test inspection under the conditions set in the past and conditions slightly varied around those conditions is automatically carried out based on control of the overall control unit 16, and an optimal value is automatically selected, or selected by the user.

In addition, an evaluation function is prepared for each process of a wafer to be inspected, and is stored, for example in the storage device or the memory (not shown) connected to the overall control unit 16, and then the overall control unit 16 can set a test condition matching the evaluation function. A rule is made beforehand and stored, for example in a storage device or a memory (not shown) connected to the overall control unit 16. Then, for example in order to slightly more improve a result obtained for one evaluation item under a given optical system condition, the overall control unit 16 can narrow down conditions from an obtained evaluation result in accordance with the rule, for example a given optical condition is varied in a given manner.

Even without any past conditions or rules, the overall control unit 16 can narrow down conditions completely automatically so as to approach an acceptance value (ideal form of radar chart) of a set evaluation item. In the case of the completely automatic operation, no intermediate results or evaluation results may be displayed at all.

Thus, actual inspection is carried out after the inspection condition has been decided. In the bright field optical inspection apparatus of the invention, the overall control unit 16 displays inspection sensitivity (inspection performance) in real time on the user interface unit 17 during inspection. The inspection sensitivity indicates, for example detection performance of positional deviation in comparative inspection, sensitivity of current inspection, a ratio of nuisance defect, a type of defects, contrast, a density difference or the like. Accordingly, it can be verified whether or not the selected test condition correctly functions immediately after a start of inspection.

The embodiment of the present invention has been described regarding the optical system condition extracting method in the DUV bright field optical inspection apparatus, in which the semiconductor wafer is a target for inspection. However, the invention can also be applied to optical system condition extraction in pattern inspection or optical inspection of charged particle type such as electron beams. A target for inspection is not limited to the semiconductor wafer, and the invention can be applied to any needing test condition (inspection condition) setting. Moreover, as well as the optical system conditions, the present invention can be applied to automatic setting of image processing parameters (especially, determination threshold value).

The above-described embodiments can provide the following advantages.

First, it is possible to reduce binding hours of the user by performing a series of test inspection while automatically changing setting for a plurality of optical system conditions set beforehand by the user.

It is possible even for an unskilled user to easily and surely select an optimal condition by quantitatively displaying side by side an image, contrast, a luminance distribution and the like for a pattern or a defect specified by the user under each test condition.

It is always possible to achieve inspection with high sensitivity without any individual differences by automatically selecting an optimal test condition.

It is possible to obtain highest sensitivity by automatically identifying a defect/nuisance defect from a result of a series of test inspection, displaying a classification result thereof on a map, and then automatically selecting a condition of a low nuisance defect ratio.

Thus, when a plurality of similar inspecting apparatus are present, it is possible to reduce sensitivity difference between the defect inspecting apparatus.

Furthermore, since inspection performance (inspection sensitivity) is displayed in real time during inspection under a set test condition, it is possible to immediately verify whether the set test condition has been correct or not.

It should be further understood by those skilled in the art that the foregoing description has been made on embodiments of the invention and that various changes and modifications may be made in the invention without departing from the spirit of the invention and scope of the appended claims.

What is claimed is:

1. A method for inspecting defects, adapted to perform a series of test inspection for detecting emitted light from a substrate to be inspected by irradiating the substrate to be inspected with light, converting the emitted light into an image signal, and discovering a defect portion on the substrate to be inspected based on a digital image signal obtained by subjecting the converted image signal to A/D conversion, while changing a plurality of test conditions comprising a deflection setting, a wavelength range, power of light setting, and an image magnification which are set beforehand, wherein, as a result of the series of test inspections, images of the defect portion discovered on the substrate to be inspected under the respective test conditions are displayed side by side on a screen along with image features including contrast, a density difference metric, and a luminescence distribution for the plurality of test conditions, wherein, as a result of the series of test inspection, bits of information of the defect portion discovered on the substrate to be inspected under the respective test conditions are presented side by side for the plurality of test conditions, and an optimal test condition is selected based on the presented bits of information of the defect portion.

2. The method for inspecting defects according to claim 1, wherein inspection performance is further presented in real time during inspection after the selection of the optimal test condition.

3. A method for inspecting defects, adapted to perform a series of test inspection for detecting emitted light from a substrate to be inspected by irradiating the substrate to be inspected with light, converting the emitted light into an image signal, and discovering a defect portion on the substrate to be inspected based on a digital image signal obtained by subjecting the converted image signal to A/D conversion, while changing a plurality of test conditions comprising a deflection setting, a wavelength range, power of light setting, and an image magnification which are set beforehand, wherein, as a result of the series of test inspections, images of the defect portion discovered on the substrate to be inspected under the respective test conditions are displayed side by side on a screen along with image features including contrast, a density difference metric, and a luminescence distribution for the plurality of test conditions, wherein, as a result of the series of test inspection, the defect portion including a nuisance defect is classified based on the digital image signal of the defect portion discovered under each test condition, and results of the classification are presented side by side for the plurality of test conditions.

4. The method for inspecting defects according to claim 3, wherein, as a result of the series of test inspection, a true defect part and a nuisance defect are identified based on the digital image signal of the defect portion discovered under each test condition, and results of the identification are presented side by side for the plurality of test conditions.

5. The method for inspecting defects according to claim 3, wherein, as a result of the series of test inspection, a true defect part and a nuisance defect are identified based on the digital image signal of the defect portion discovered under each test condition, and the identified test condition having a low nuisance defect ratio is selected.

6. A method for inspecting defects, comprising steps of:
obtaining an image of a specimen by irradiating the specimen with light using a first irradiation condition including a deflection condition, a wavelength region, and a power setting, and detecting light reflected from the specimen with a sensor with a first detection condition including an image magnification and a scanning speed of the sensor;
extracting a feature of the obtained image;
repeating the steps of obtaining and extracting by changing a test condition which includes the first irradiation condition and the first detection condition; and
displaying plural images side by side which correspond to the test conditions obtained by the obtaining step, each of the images being accompanied with the features extracted at the extracting step including contrast, a density difference, and a luminance distribution.

7. A method according to the claim 6, further comprising a step of detecting defects from the obtained image, and the features of the obtained image in the step of extracting includes a feature of an image of the detected defect.

8. A method for inspecting defects, comprising steps of:
obtaining an image of a specimen by irradiating the specimen with light using a first irradiation condition including a deflection condition, a wavelength region, and a power setting, and detecting light reflected from the specimen with a sensor with a first detection condition including an image magnification and a scanning speed of the sensor;
extracting features of the obtained image;
detecting defects from the obtained image;
classifying the detected defects into plural classes;
repeating the steps of obtaining, extracting, detecting, and classifying by changing the first irradiation condition and the first detection condition; and
displaying plural images side by side, each of which indicates distribution of the classified defects on the specimen corresponding to each of the irradiation condition and the detection condition obtained by the obtaining step and each of which is accompanied with information including one of a ratio of false defects to a total number of defects, a number of foreign particles, a number of shape failures, and a number of scratches for each of the classes.

9. A method according to the claim 8, in the step of displaying, percentage of each defect class is displayed in association with the distribution.

10. An apparatus for inspecting defects, comprising:
an imager which obtains an image of a specimen by irradiating the specimen with light using an irradiation condition including a deflection condition, a wavelength region, and a power setting, and detecting light reflected from the specimen with a sensor with a detection condition including an image magnification and a scanning speed of the sensor;
an processor which processes the image obtained by the imager and extracts features of the image;
a controller which controls the imager and the processor to repeat obtaining the image of the specimen and processing the image to extracts features of the image by changing a test condition which includes the irradiation condition and the detection condition; and
a display which displays plural images side by side, the images corresponding to the test conditions obtained, wherein each of the images is accompanied with the features extracted by the processor including contrast, a density difference, and a luminance distribution.

11. An apparatus according to the claim 10, wherein the processor further detects defects from the obtained image, and the extracted feature of the obtained image is a feature of an image of the detected defect.

12. An apparatus for inspecting defects, comprising:
an imager which obtains an image of a specimen by irradiating the specimen with light using an irradiation condition including a deflection condition, a wavelength region, and a power setting, and detecting light reflected from the specimen with a sensor with a detection condition including an image magnification and a scanning speed of the sensor;
a first processor which extracts features of the image obtained by the imager;
a second processor which detects defects with a detecting condition from the image obtained by the imager;
a third processor which classifies the defects detected by the second processor into plural classes;
a controller which controls the imager, the first processor, the second processor, and the third processor to repeat obtaining, extracting, detecting, and classifying by changing at least one of the irradiation condition, the detection condition, or the detecting condition; and
a display which displays plural images side by side, each of which indicates distribution of the classified defects on the specimen corresponding to each of the irradiation condition and the detection condition and each of which is accompanied with information including one of a ratio of false defects to a total number of defects, a number of foreign particles, a number of shape failures, and a number of scratches for each of the classes.

13. An apparatus according to the claim 12, wherein the display displays a percentage of each defect class in association with the distribution of the classified defects.

14. A method for inspecting defects comprising steps of:
performing a series of test inspections to determine a set of inspection conditions for detecting defects;
inspecting a specimen using the set of inspection conditions by irradiating light onto the specimen, capturing an image of the specimen by detecting light reflected from the specimen, and processing the captured image; and
detecting defects of the specimen from the processed captured image,
wherein in the step of performing a series of test inspection:
test conditions including at least one of a deflection setting of light that is used to irradiate a test sample and of reflected light that is reflected from the sample, a wavelength range of the irradiating light, a power setting of the irradiating light, or a magnification setting of the image are changed for each test inspection; and images of defects detected on the sample under the respective test conditions are displayed side by side on a screen along with an identification of the respective test conditions and along with image features including at least one of a contrast level, a density difference, or a luminescence distribution of the respective test conditions.

15. The method for inspecting defects according to claim 14, wherein the information of the defect portion is represented by a defect map indicating a defect portion distribution.

16. The method for inspecting defects according to claim 15, wherein coincidence of defect portions between the test conditions is further presented.

17. The method for inspecting defects according to claim 14, wherein the information of the defect portion is a combination of a plurality of any selected from an image, contrast, brightness or a density difference, and a luminance distribution of a specified defect portion.

18. The method for inspecting defects according to claim 14, wherein bits of information regarding digital image signals of a specified region among the digital image signals obtained under the respective test conditions are further presented side by side for a plurality of test conditions.

19. The method for inspecting defects according to claim 14, wherein the information regarding the digital image signal of the specified region is a combination of a plurality of any selected from an image, contrast, brightness and a luminance distribution.

* * * * *

UNITED STATES PATENT AND TRADEMARK OFFICE
CERTIFICATE OF CORRECTION

PATENT NO. : 6,879,392 B2
DATED : April 12, 2005
INVENTOR(S) : Kaoru Sakai et al.

It is certified that error appears in the above-identified patent and that said Letters Patent is hereby corrected as shown below:

<u>Title page,</u>
Item [30], Foreign Application Priority Data, should read as:
-- [30]   Foreign Application Priority Data
    April 3, 2001        (JP)           2001-104153 --

Signed and Sealed this

Twelfth Day of July, 2005

JON W. DUDAS
*Director of the United States Patent and Trademark Office*